(12) United States Patent
Ishida et al.

(10) Patent No.: US 12,114,979 B2
(45) Date of Patent: Oct. 15, 2024

(54) BIOMAGNETIC FIELD MEASUREMENT PROCESSING APPARATUS, BIOMAGNETIC FIELD MEASUREMENT SYSTEM, AND CONTROL METHOD OF BIOMAGNETIC FIELD MEASUREMENT PROCESSING APPARATUS

(71) Applicants: Koki Ishida, Kanagawa (JP); Taishi Watanabe, Tokyo (JP); Shigenori Kawabata, Tokyo (JP); Jun Hashimoto, Tokyo (JP)

(72) Inventors: Koki Ishida, Kanagawa (JP); Taishi Watanabe, Tokyo (JP); Shigenori Kawabata, Tokyo (JP); Jun Hashimoto, Tokyo (JP)

(73) Assignees: Ricoh Company, Ltd., Tokyo (JP); National University Corporation Tokyo Medical and Dental University, Tokyo (JP)

( * ) Notice: Subject to any disclaimer, the term of this patent is extended or adjusted under 35 U.S.C. 154(b) by 266 days.

(21) Appl. No.: 17/663,720

(22) Filed: May 17, 2022

(65) Prior Publication Data
US 2022/0369982 A1    Nov. 24, 2022

(30) Foreign Application Priority Data
May 19, 2021  (JP) .................. 2021-084530

(51) Int. Cl.
*A61B 5/242*   (2021.01)
*A61B 5/00*   (2006.01)
(Continued)

(52) U.S. Cl.
CPC .............. *A61B 5/242* (2021.01); *A61B 5/743* (2013.01); *A61N 1/0456* (2013.01); *G09G 5/37* (2013.01); *G09G 2380/08* (2013.01)

(58) Field of Classification Search
CPC ........... A61B 5/05; A61B 5/242; A61B 5/248; A61B 5/388; A61B 5/4029; A61B 5/743;
(Continued)

(56) References Cited

U.S. PATENT DOCUMENTS

2017/0347908 A1   12/2017   Watanabe et al.
2018/0008223 A1*   1/2018   Yamagata ............ A61B 6/5211
(Continued)

FOREIGN PATENT DOCUMENTS

EP         3646782        5/2020
JP       2017-217443     12/2017
(Continued)

OTHER PUBLICATIONS

Sumiya et al., "Magnetospinography visualizes electrophysiological activity in the cervical spinal cord", 2017, Scientific Reports (Year: 2017).*

(Continued)

*Primary Examiner* — Katherine L Fernandez
*Assistant Examiner* — Brooke Lyn Klein
(74) *Attorney, Agent, or Firm* — IPUSA, PLLC

(57) ABSTRACT

A biomagnetic field measurement processing apparatus includes circuitry; and a memory storing computer-executable instructions that cause the circuitry to execute reconfiguring a current signal from a biomagnetic field signal; extracting a current component from the current signal; and based on the extracted current component, adding to each other at least two current waveforms among current waveforms of a plurality of inward currents that are current components directed toward a nerve axon from around the nerve axon, or adding to each other at least two current waveforms among current waveforms of a plurality of inward currents that are current components directed toward a muscle fiber from around the muscle fiber, and generating (Continued)

a current waveform to be displayed on a display device, according to the at least two current waveforms added to each other.

6 Claims, 12 Drawing Sheets

(51) Int. Cl.
*A61N 1/04* (2006.01)
*G09G 5/37* (2006.01)

(58) Field of Classification Search
CPC ............... A61N 1/0452; A61N 1/0456; A61N 1/36034; G09G 2380/08; G09G 5/37; G09G 5/377
See application file for complete search history.

(56) References Cited

U.S. PATENT DOCUMENTS

| | | | |
|---|---|---|---|
| 2020/0411180 A1* | 12/2020 | Kinoshita | A61B 5/742 |
| 2021/0113141 A1* | 4/2021 | Ikeda | A61B 5/0035 |
| 2021/0158780 A1 | 5/2021 | Takahashi et al. | |

FOREIGN PATENT DOCUMENTS

| | | |
|---|---|---|
| JP | 2020-092982 | 6/2020 |
| JP | 2021-083479 | 6/2021 |
| JP | 2021-087756 | 6/2021 |
| WO | 2021/106948 | 6/2021 |

OTHER PUBLICATIONS

Shuta Ushio et al., "Non-invasive functional evaluation of cauda equina in middle-aged subjects by magnetospinography", The Journal of Japan Biomagnetism and Bioelectromagnetics Society, Special edition, vol. 28, No. 1, 2015, 30th Japan Biomagnetism and Bioelectromagnetics Society collection of papers, with English Abstract.

Senichi Ishii et al., "Conductive neuromagnetic fields in the lumbar spinal canal", Clinical Neurophysiology, vol. 123 (2012), 1656-1661.

U.S. Appl. No. 17/654,629, filed Mar. 14, 2022.

* cited by examiner

FIG.4
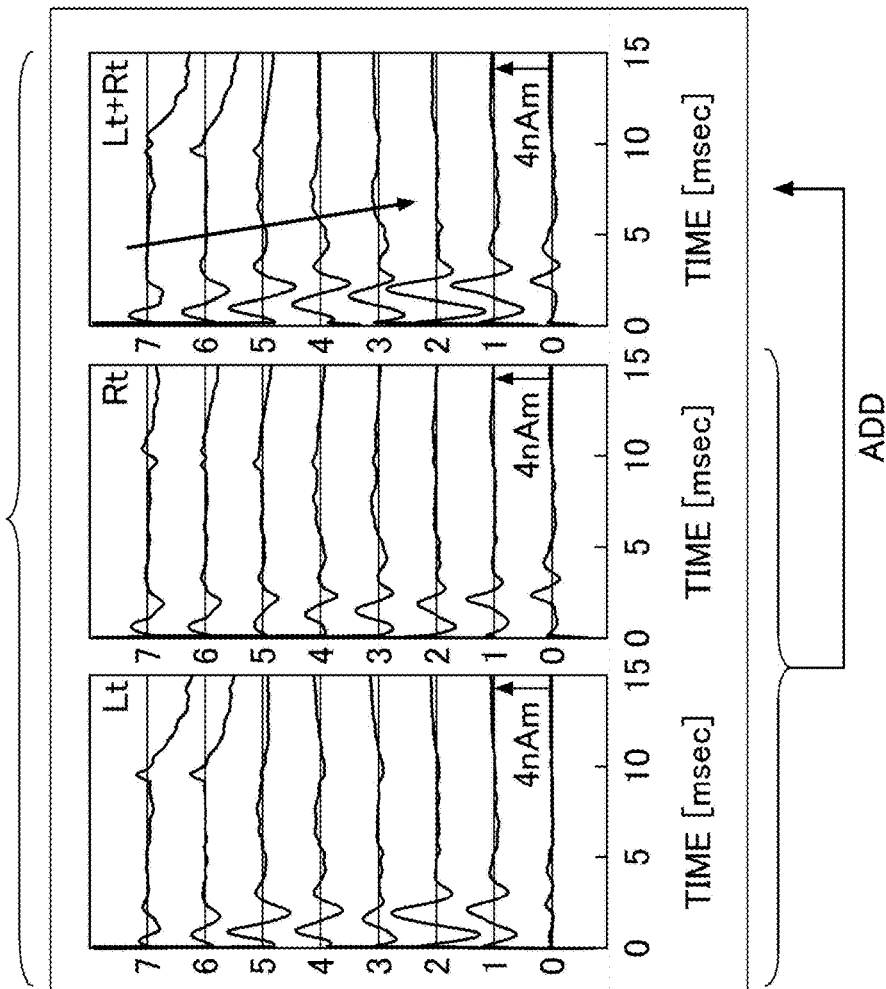
CURRENT WAVEFORM INDICATING CONDUCTION OF INWARD CURRENT
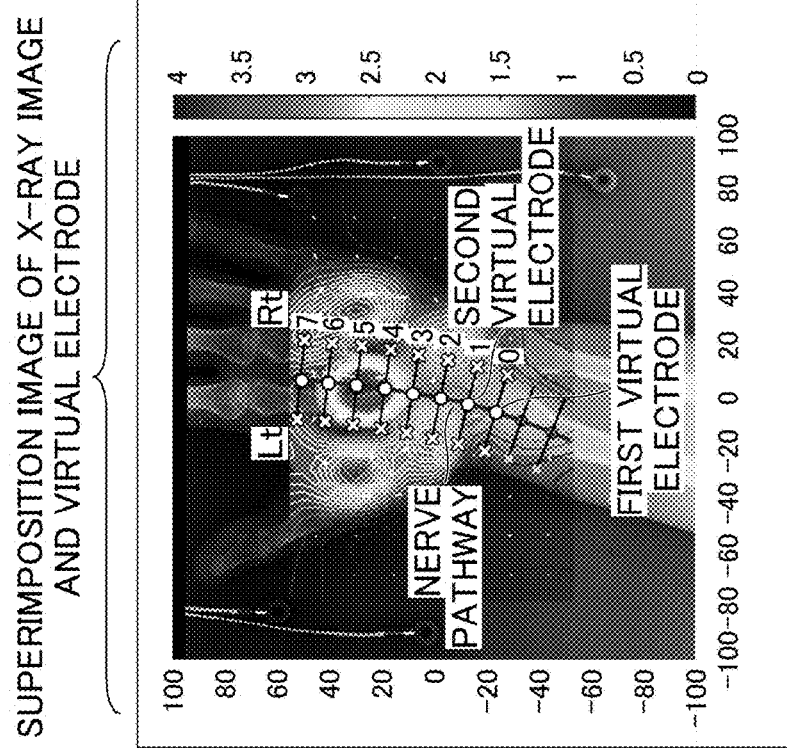
SUPERIMPOSITION IMAGE OF X-RAY IMAGE AND VIRTUAL ELECTRODE

BIOMAGNETIC FIELD MEASUREMENT PROCESSING APPARATUS, BIOMAGNETIC FIELD MEASUREMENT SYSTEM, AND CONTROL METHOD OF BIOMAGNETIC FIELD MEASUREMENT PROCESSING APPARATUS

CROSS-REFERENCE TO RELATED APPLICATION

The present application is based on and claims priority under 35 U.S.C. § 119 to Japanese Patent Application No. 2021-084530, filed on May 19, 2021, the contents of which are incorporated herein by reference in their entirety.

BACKGROUND OF THE INVENTION

1. Field of the Invention

The present invention relates to a biomagnetic field measurement processing apparatus, a biomagnetic field measurement system, and a control method of the biomagnetic field measurement processing apparatus.

2. Description of the Related Art

A biomagnetic field measurement processing apparatus estimates the electric current distribution in the body of a subject by using a spatial filter method based on the magnetic field data obtained from the measurement of the biomagnetic field by a magnetic field measurement apparatus. Then, for example, the biomagnetic field measurement processing apparatus generates a current waveform on a plurality of virtual electrodes arranged along the spinal canal in a morphological image of a part to be measured of the subject based on the estimated current distribution, and displays the generated current waveform on a display device. This enables the visualization of the electrical activity at any point in the body.

For example, the neural activity can be divided into an intracellular current, which is a current component generated along a nerve axon, and a volume current, which is a current component generated by depolarization. The volume current flows out of the nerve axon and returns to the depolarization point. The intracellular current is also referred to as an intra-axonal current (current in the axon), and the volume current returning to the depolarization point is also referred to as inward current.

Non-patent Document 1: Shuta USHIO et al., "Non-invasive functional evaluation of cauda equina in middle-aged subjects by magnetospinography", The Journal of Japan Biomagnetism and Bioelectromagnetics Society, Special edition, Vol. 28, No. 1, 2015, 30th Japan Biomagnetism and Bioelectromagnetics Society collection of papers Non-patent Document 2: Senichi Ishii et al, "Conductive neuromagnetic fields in the lumbar spinal canal", Clinical Neurophysiology, Volume 123 (2012), 1656-1661

SUMMARY OF THE INVENTION

According to one aspect of the present invention, there is provided a biomagnetic field measurement processing apparatus including circuitry; and a memory storing computer-executable instructions that cause the circuitry to execute reconfiguring a current signal from a biomagnetic field signal; extracting a current component from the current signal; and based on the extracted current component, adding to each other at least two current waveforms among current waveforms of a plurality of inward currents that are current components directed toward a nerve axon from around the nerve axon, or adding to each other at least two current waveforms among current waveforms of a plurality of inward currents that are current components directed toward a muscle fiber from around the muscle fiber, and generating a current waveform to be displayed on a display device, according to the at least two current waveforms added to each other.

BRIEF DESCRIPTION OF THE DRAWINGS

FIG. 4 is a diagram illustrating an example of the change of the current waveform of the inward current in the palmar part of the carpal tunnel when a stimulation is applied simultaneously to the index finger and middle finger of a subject (healthy person) and the summed waveform according to an embodiment of the present invention;

DESCRIPTION OF THE EMBODIMENTS

Figure 1:
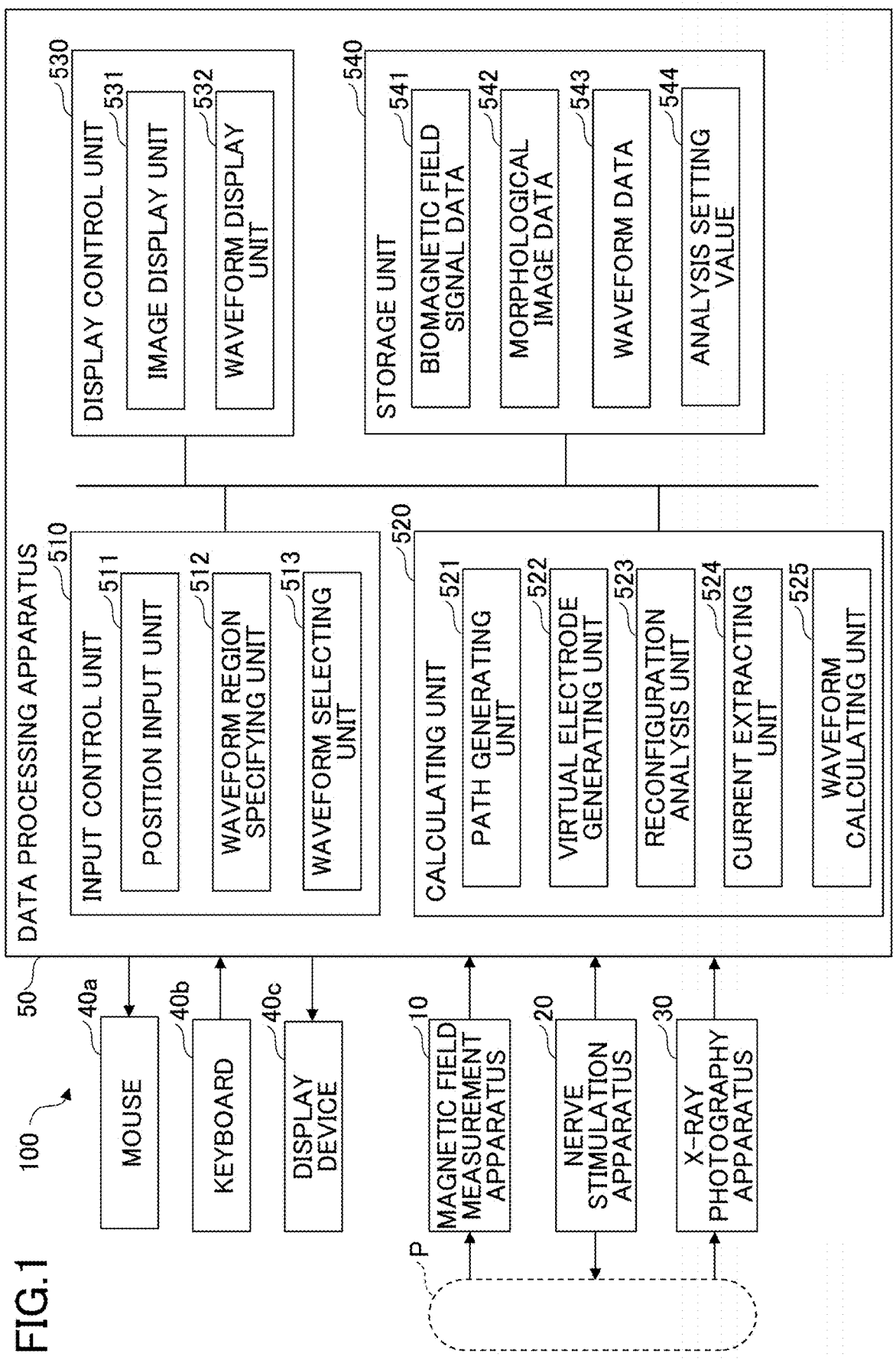
FIG. 1 is a block diagram illustrating an example of a biomagnetic field measurement system including a biomagnetic field measurement processing apparatus according to an embodiment of the present invention.

When the current distribution to be estimated is affected by tissue such as the bone around the part to be evaluated, the inward current generated based on the current distribution may be biased, and the current waveform may be distorted. The current waveform of the inward current is used as an indicator of the evaluation of the neural function, and, therefore, distortion in the current waveform can lead to underestimation or overestimation of the neural function.

A problem to be addressed by an embodiment of the present invention is to generate a current waveform of the inward current that can be used to properly evaluate the neural function or the muscle function even when the current waveform of the inward current is distorted by the influence of the tissue surrounding the part being evaluated.

Hereinafter, embodiments will be described with reference to the drawings. In each drawing, the same elements are denoted by the same reference numerals and overlapping descriptions may be omitted.

First Embodiment

FIG. 1 is a block diagram illustrating an example of a biomagnetic field measurement system including a biomagnetic field measurement processing apparatus according to a first embodiment of the present invention. A biomagnetic field measurement system 100 illustrated in FIG. 1 includes a magnetic field measurement apparatus 10, a nerve stimulation apparatus 20, an X-ray photography apparatus 30, a mouse 40a, a keyboard 40b, a display device 40c, and a data processing apparatus 50 that functions as a biomagnetic field measurement processing apparatus.

For example, the magnetic field measurement apparatus 10 includes a superconducting quantum interference device (SQUID) sensor array including a plurality of SQUIDs and a signal processing apparatus. The magnetic field measurement apparatus 10 is capable of measuring the biomagnetic field induced in the nerve or muscle that is the measurement target of a subject P by electrical stimulation by the nerve stimulation apparatus 20.

For example, the magnetic field measurement apparatus 10 may be used as a spinal magnetometer (MSG: Magnetospinograph) or a muscle magnetometer (MMG: Magnetomyograph). The magnetic field measurement apparatus 10 may be used as a brain magnetometer (MEG: Magnetoencephalography) or a cardiographic magnetometer (MCG: Magnetocardiograph). Hereinafter, a superconducting quantum interference device is also referred to as SQUID.

The nerve stimulation apparatus 20 electrically stimulates the nerves or muscles of the subject P through electrodes attached to the body surface (skin) of the subject P. The X-ray photography apparatus 30 captures a morphological image of the part of the subject P where the biomagnetic field is to be measured. Note that, when measuring the muscle-induced biomagnetic field of the subject P, an MRI (Magnetic Resonance Imaging) apparatus may be used instead of the X-ray photography apparatus 30. Alternatively, a morphological image of the subject P may be captured by using both the X-ray photography apparatus 30 and an MRI apparatus that is not illustrated.

The data processing apparatus 50 has a function for controlling the timing and the like of electrical stimulation to the body by the nerve stimulation apparatus 20 and a function for performing information processing of biological information such as a biomagnetic field measured by the magnetic field measurement apparatus 10. The data processing apparatus 50 also has a function for controlling the capturing of an X-ray image of the subject P by the X-ray photography apparatus 30. The data processing apparatus 50 functions to receive inputs from input/output devices such as the mouse 40a and the keyboard 40b.

The data processing apparatus 50 has a function of superimposing the direction of the current generated according to the magnetic field measured by the magnetic field measurement apparatus 10, on an X-ray image, and displaying the superimposed image on the display device 40c. The data processing apparatus 50 has the function of calculating the change of the current value over time at a plurality of continuous positions (virtual electrodes) instructed by an operator operating the mouse 40a with respect to an image displayed on the display device 40c.

For example, the operator may use the mouse 40a to input a plurality of positions along the peripheral nerves or muscles (e.g., the intrinsic muscles or the tibialis anterior muscle) recognized in an X-ray image displayed on the screen of the display device 40c. The data processing apparatus 50 functions to generate a curve, such as a Bezier curve along peripheral nerves or muscles, based on a plurality of the input positions, and to generate a plurality of virtual electrodes along the curve, based on predetermined setting values. The data processing apparatus 50 further functions to display the current waveform at each virtual electrode on the display device 40c.

The data processing apparatus 50 includes an input control unit 510, a calculating unit 520, a display control unit 530, and a storage unit 540. For example, the functions of the input control unit 510, the calculating unit 520, and the display control unit 530 are implemented by a control program executed by a processor such as a Central Processing Unit (CPU) installed in the data processing apparatus 50.

The input control unit 510, the calculating unit 520, and the display control unit 530 may be implemented by hardware, such as a field-programmable gate array (FPGA), or may be implemented by a combination of software and hardware.

For example, the storage unit 540 may be implemented by at least one of a Dynamic Random Access Memory (DRAM), a Static Random Access Memory (SRAM), a Read Only Memory (ROM), and a semiconductor storage device such as a flash memory. The storage unit 540 may be implemented by including a semiconductor storage device and a hard disk drive (HDD) or a solid state drive (SSD).

The input control unit 510 includes a position input unit 511, a waveform region specifying unit 512, and a waveform selecting unit 513. The calculating unit 520 includes a path generating unit 521, a virtual electrode generating unit 522, a reconfiguration analysis unit 523, a current extracting unit 524, and a waveform calculating unit 525. The display control unit 530 includes an image display unit 531 and a waveform display unit 532. The storage unit 540 is allocated a storage area for storing biomagnetic field signal data 541, morphological image data 542, waveform data 543, and an analysis setting value 544.

The input control unit 510 receives an operation of the mouse 40a, the keyboard 40b, and the like, by an operator of the magnetic field measurement apparatus 10. The input of information by an operation of the mouse 40a, the keyboard 40b, and the like is an example of external input. The position input unit 511 receives the position of the peripheral nerve or the position of muscle fiber that is used to evaluate the biomagnetic field in a morphological image, such as an X-ray image, displayed on the screen of the display device 40c. The position information received by the position input unit 511 is stored in the storage unit 540 as the analysis setting value 544.

The waveform region specifying unit 512 receives a time range in which the current waveform on the virtual electrode is displayed on the display device 40c. The waveform selecting unit 513 selects the current waveform to be displayed on the display device 40c based on an operation of the mouse 40a, the keyboard 40b, and the like. The waveform selecting unit 513 selects the current waveforms to be added to each other, among the current waveforms displayed on the display device 40c, based on an operation of the mouse 40a, the keyboard 40b, and the like. Further, the waveform selecting unit 513 selects the current waveforms to be superimposed and displayed, among the current waveforms displayed on the display device 40c, based on an operation of the mouse 40a, the keyboard 40b, and the like.

The path generating unit 521 calculates the path of the peripheral nerve or muscle fiber based on positional information indicating the positions of a plurality of peripheral nerves or the positions of a plurality of muscle fibers on the morphological image, input from the position input unit 511. Because the techniques for measuring the biomagnetic fields of peripheral nerves and muscle fibers are the same, the following discussion will describe an example of measuring the biomagnetic fields of mainly peripheral nerves. Hereinafter, the path of the peripheral nerve calculated by the path generating unit 521 is also referred to as the nerve travel (path). Here, the path of the peripheral nerve calculated by the path generating unit 521 is represented by a plurality of pieces of coordinate information or an equation representing a curve or the like, and is stored in the storage unit 540 as the analysis setting value 544.

The virtual electrode generating unit 522 generates, for example, a plurality of first virtual electrodes at regular intervals, on the nerve pathway calculated by the path generating unit 521. Further, the virtual electrode generating unit 522 generates the second virtual electrodes in the orthogonal direction on respective sides of the travel direction of the nerve pathway with respect to the first virtual electrodes.

The number and the intervals of the first virtual electrodes generated on the nerve pathway, and the distance from the first virtual electrode to the second virtual electrode, are previously input by an operator via an input device such as the mouse 40a or the keyboard 40b. The position information of the first virtual electrode and the second virtual electrode is stored in the storage unit 540 as the analysis setting value 544 by the input control unit 510. Hereinafter, when the first virtual electrode and the second virtual electrode are described without distinction, these are simply referred to as virtual electrodes.

The reconfiguration analysis unit 523 reconfigures a current component (current signal) for each voxel arranged in a matrix at predetermined intervals, by using the biomagnetic field data (biomagnetic field signal) of the subject P obtained by the measurement of the biomagnetic field by the magnetic field measurement apparatus 10. The voxel is described with reference to FIG. 2.

The current extracting unit 524 extracts the current components of each virtual electrode by using the current component of the voxel calculated by the reconfiguration analysis unit 523 based on the positional relationship between each virtual electrode and the voxel. For example, the current extracting unit 524 extracts the current component (assuming the head side is positive and the tail side is negative) at the first virtual electrode along the nerve pathway as the intra-axonal current that is conducted through the nerve axon in the nerve pathway, within the time range received by the waveform region specifying unit 512. The current extracting unit 524 extracts, as the inward current, the current component directed toward the nerve axon as from the second virtual electrode positioned around the nerve axon, within the time range received by the waveform region specifying unit 512.

The waveform calculating unit 525 generates a current waveform representing the change over time of an intra-axonal current in the first virtual electrode extracted by the current extracting unit 524. The waveform calculating unit 525 generates a current waveform representing the change over time of the inward current in the second virtual electrode extracted by the current extracting unit 524. Among the volume currents flowing outside the nerve axon, the inward current, which is a current component flowing into the depolarization point, is important in evaluating the neural function.

Figure 5:
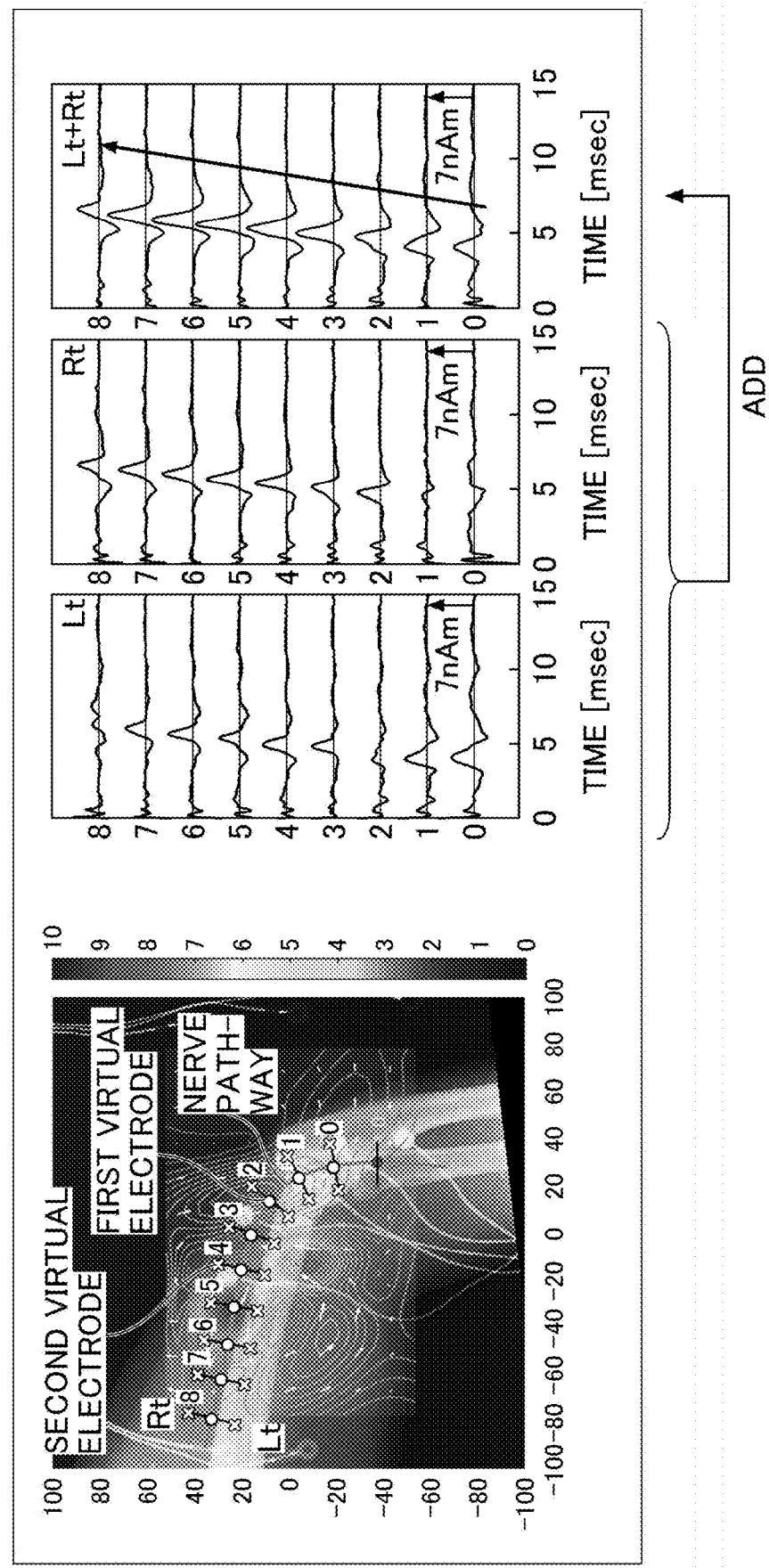
FIG. 5 is a diagram illustrating an example of a change in the current waveform of an inward current in the cubital tunnel when a stimulation is applied to the ulnar nerve of a subject (healthy person) and a summed waveform according to an embodiment of the present invention.
Figure 6:
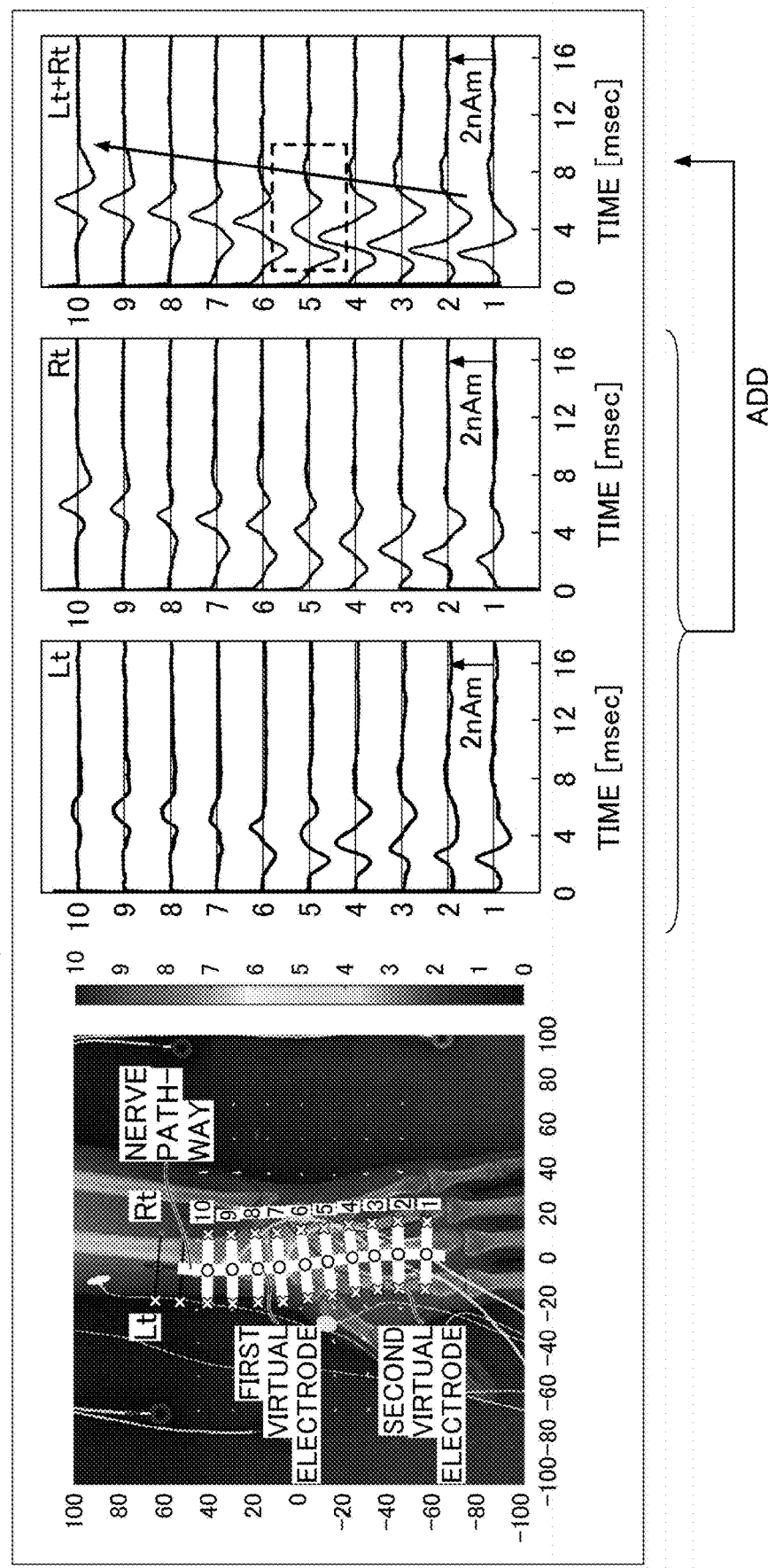
FIG. 6 is a diagram illustrating the change in the current waveform of the inward current in the palmar part of the carpal tunnel when a stimulation is applied simultaneously to the index and middle fingers of the subject (patient) and the summed waveform according to an embodiment of the present invention.

As illustrated in FIGS. 4 to 6 below, the image display unit 531 superimposes a small white arrow representing the direction and the intensity of the current in each voxel reconfigured by the reconfiguration analysis unit 523, on a morphological image (X-ray image), and causes the display device 40c to display the superimposed image. As illustrated in FIGS. 4 to 6, the image display unit 531 superimposes the nerve pathway calculated by the path generating unit 521 and the virtual electrodes generated by the virtual electrode generating unit 522 on an X-ray image and causes the display device 40c to display the superimposed image.

The waveform display unit 532 arranges the current data values of the intra-axonal current and the current data values of the inward current in time sequence to generate the current waveform which represents the change over time of the intra-axonal current and the inward current at the virtual electrodes, as image data. The waveform display unit 532 causes the display device 40c to display the generated current waveform of each virtual electrode in association with the virtual electrode superimposed on the X-ray image.

The storage area of the biomagnetic field signal data 541 stores the magnetic field data obtained by measuring the magnetic field generated from the subject P, by the magnetic field measurement apparatus 10. The storage area of the morphological image data 542 stores the X-ray image data of the part of the subject P where the magnetic field is to be measured, captured by the X-ray photography apparatus 30.

In the storage area of the analysis setting value 544, various parameters required for the measurement of the biomagnetic field by the magnetic field measurement apparatus 10 and various setting values such as filters (high-pass filters and low-pass filters) used for the magnetic field data obtained by the measurement of the biomagnetic field, are stored in advance. In the storage area of the analysis setting value 544, position information representing the position of the voxel which is the calculation point of the current in the image displayed on the display device 40c and the position of the virtual electrode for acquiring the current waveform, etc., are stored in advance.

Figure 2:
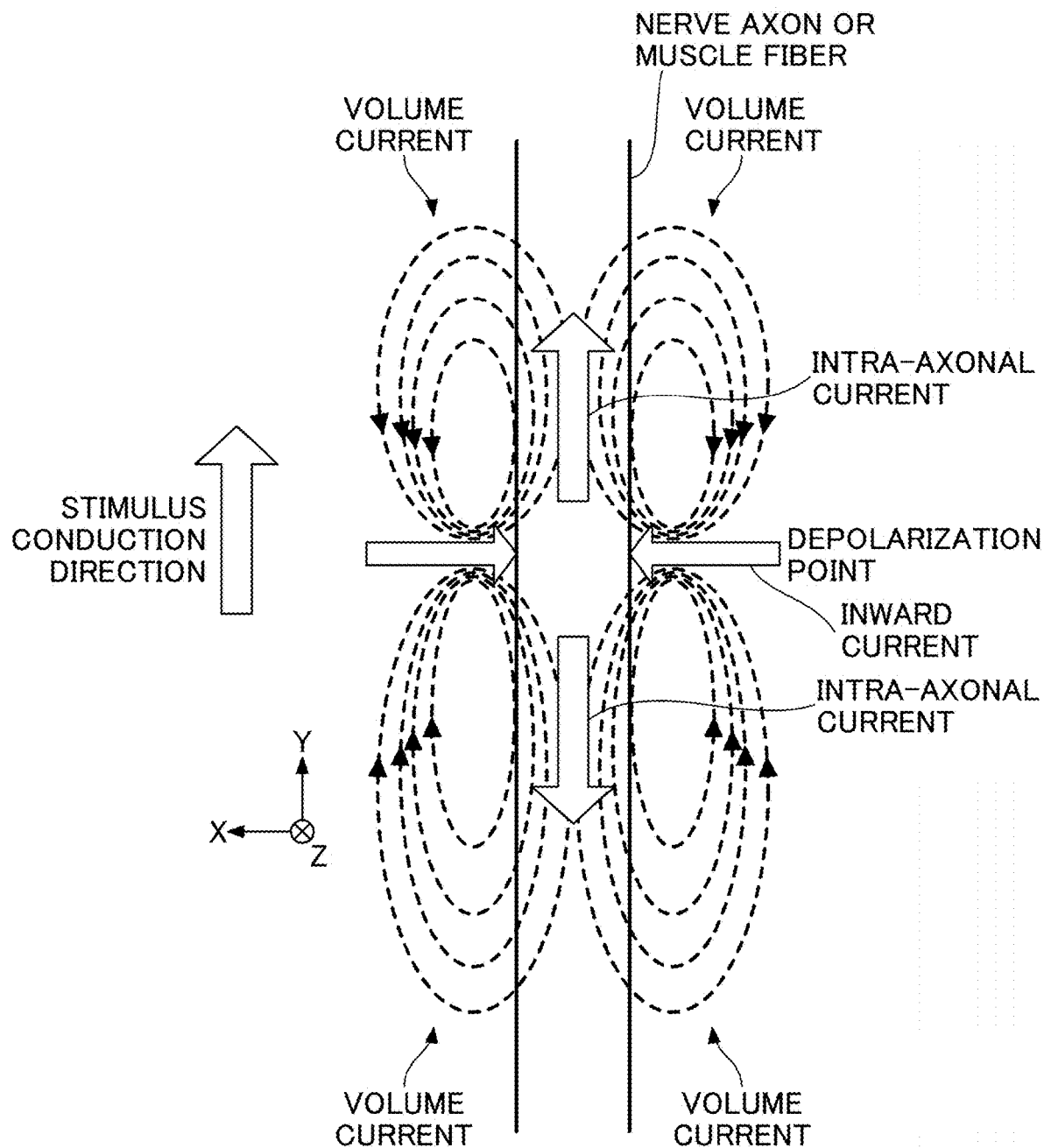
FIG. 2 is an explanatory diagram illustrating an example of a model of a neural/muscle activity current according to an embodiment of the present invention.

FIG. 2 is an explanatory diagram illustrating an example of a model of a neural/muscle activity current. Because the model of a neural activity current and a model of a muscle activity current are similar to each other, the model of a neural activity current is described below.

FIG. 2 illustrates how current is generated by neural activity traveling linearly in a vertical direction in the figure, with the lower side of FIG. 2 being the peripheral side and the upper side of FIG. 2 being the central side. For example, by applying electrical stimulation to the peripheral nerve, the stimulation is conducted as an electrical current in the nerve axon from the bottom to the top.

In this case, an intra-axonal current flowing upward (forward) in FIG. 2 and an intra-axonal current flowing downward (backward) in FIG. 2, and a volume current that is a current component flowing outward from the nerve axon and returning to the depolarization point, are generated. The intra-axonal current flowing upwardly in FIG. 2 is referred to as the leading component, and the intra-axonal current flowing downwardly in FIG. 2 is referred to as the trailing component.

For further evaluation of the neural function, for example, the current extracting unit 524 extracts the current component of the intra-axonal current flowing along the nerve axon and the current component of the inward current flowing into the depolarization point, based on the reconfigured current component per voxel. The intra-axonal current is the current component in the direction along the nerve pathway, and the inward current is the current component directed to the nerve axon from the surroundings of the nerve axon. For example, an inward current is a current component directed toward a nerve axon along a cross-sectional direction of the nerve axon.

When evaluating the muscle activity current, the current extracting unit 524 extracts the current component in the intra-muscle fiber current flowing in the muscle fiber along the muscle fiber and the current component of the inward current flowing into the depolarization point. The intra-muscle fiber current is a current component flowing in the muscle fiber along the muscle fiber, and the inward current is a current component flowing from the surroundings of the muscle fiber toward the muscle fiber. For example, an inward current is a current component directed toward a muscle fiber along the cross-sectional direction of the muscle fiber.

Here, considering the principle of neural activity, the origin of the inward current is either a nerve signal that is conducted through the axon or a muscle activity signal that is conducted through the muscle fiber. Thus, the total amount of inward current flowing into the nerve is equal to the total amount of intra-axonal current flowing in the nerve axon. The total amount of inward current flowing into the muscle fiber is equal to the total amount of muscle activity current flowing in the muscle fiber. Thus, if the inward current flowing in from one direction decreases, the inward current flowing in from the other direction increases.

Figure 3:
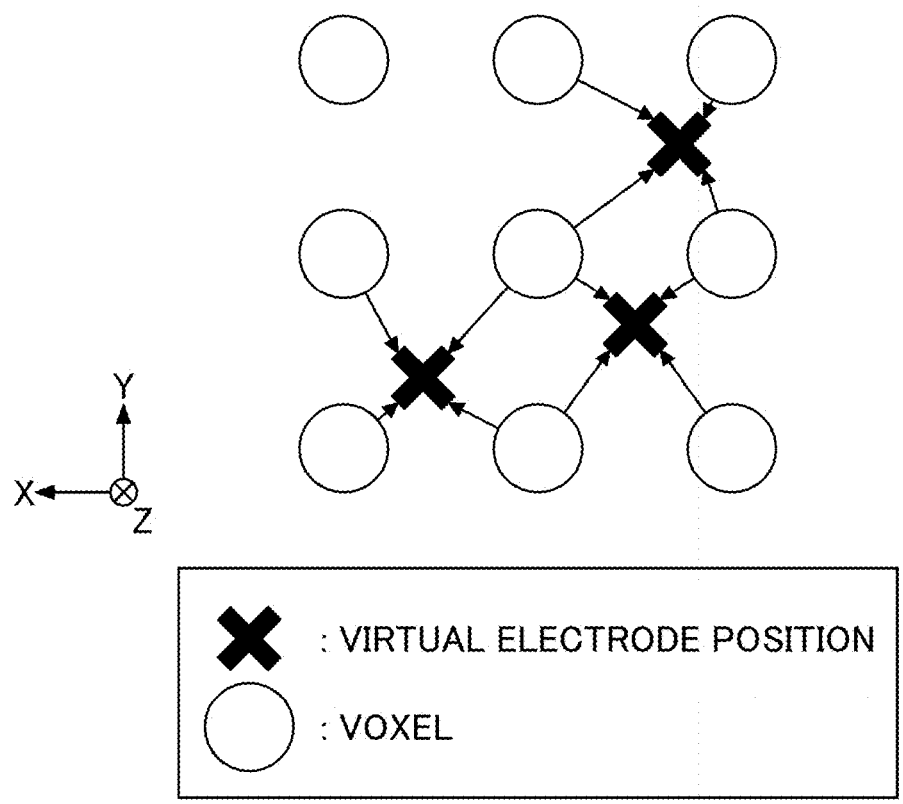
FIG. 3 is a diagram illustrating an example of a method for calculating the current intensity of a virtual electrode generated by a virtual electrode generating unit according to an embodiment of the present invention.

FIG. 3 is an explanatory diagram illustrating an example of a method of calculating the current intensity of the virtual electrode generated by the virtual electrode generating unit 522 of FIG. 1. In FIG. 3, the linear interpolation technique is used to calculate the current intensity of the virtual electrode from the intensity of the current reconfigured on voxels arranged in a matrix. With this operation, the estimated intensity of the current in the X, Y, and Z directions of the virtual electrode can be calculated.

In FIG. 3, the interval between the voxels and the interval between the virtual electrodes are set to be approximately the same for the sake of facilitating the understanding of the explanation, but in reality, the interval between the virtual electrodes may be several times larger than the interval between the voxels and can be set to any interval. Also, for example, SQUID magnetic sensors are spaced several centimeters apart while voxels are spaced several millimeters apart.

The current intensity at the virtual electrode may be calculated by a method of using the RENS (RECursive Null Steering) filter studied by the inventor of the present invention. In this case, it is possible to calculate the current intensity of each virtual electrode accurately in a short time compared to the case in which the current intensity is calculated by the linear interpolation method.

FIG. 4 is a diagram illustrating an example of a change in the current waveform of an inward current in the palmar part of the carpal tunnel when a stimulation is applied simultaneously to the index finger and the middle finger of a subject P (healthy person), and a summed waveform. On the left side of FIG. 4, a superimposed image is illustrated, in which a nerve pathway, a first virtual electrode, and a second virtual electrode are superimposed on an X-ray image of the palm of the subject P. The superimposed image also includes a small white arrow representing the direction and intensity of the current in voxels arranged in a matrix. The superimposed image also includes a current intensity distribution line (contour-like curve) indicating the positions of the same current intensity. The current intensity distribution line indicates that current is stronger as the color becomes whiter and weaker when the color becomes blacker.

In FIG. 4, the first virtual electrode is represented by a circle and the second virtual electrode is represented by an x mark. The second virtual electrodes are positioned in a cross-sectional direction with respect to the nerve axon (each first virtual electrode). Thus, it is possible to generate a current waveform of the inward current along a cross-sectional direction with respect to the nerve axon based on the current component of each second virtual electrode.

The reference symbol Lt denotes a row of the second virtual electrodes located on the thumb side of the first virtual electrodes, and the reference symbol Rt denotes a row of the second virtual electrodes located on the little finger side of the first virtual electrodes. Numbers from 0 to 7 applied to the virtual electrodes of the row Rt are the electrode numbers indicating the association with the current waveform. The electrode number of the second virtual electrode of the row Lt is the same as that of the corresponding second virtual electrode in the row Rt.

In the X-ray image, the terminals connected to the cables illustrated outside the thumb and the little finger respectively are the electrodes captured together with the subject P to associate the X-ray image (morphological image) with the magnetic field data measurement position measured by the SQUID magnetic sensor.

The right side of FIG. 4 illustrates the current waveform at the second virtual electrodes of the row Lt and the current waveform at the second virtual electrodes of the row Rt. The current waveform of each of the second virtual electrodes indicates the change over time of the inward current conducted to the nerve axon. Further, on the right side of FIG. 4, a current waveform (Lt+Rt) is illustrated, in which the current waveform of the second virtual electrode of the row Lt and the current waveform of the second virtual electrode of the row Rt are added to each other with respect to each electrode number. The downward arrow in the graph of the current waveform (Lt+Rt) indicates that the inward current is conducted from the periphery side to the central side. The numerical value at the bottom right of the three graphs of current waveforms (in this example, 4 nAm) indicates a current dipole.

The current waveform illustrated in FIG. 4 indicates the measurement result in a healthy person with no abnormalities in the nerves of the palmar part of the carpal tunnel. However, for example, the current waveforms of the electrode numbers 6, 5, and 4 in the row Lt are not normal because the amplitude peaks are matching. Further, the current waveform of the electrode number 3 of the row Lt is not normal because the peak of the amplitude is reduced.

Although the current waveforms in the row Rt are normally conducted, the amplitude of the current waveforms is unstable.

In contrast, the current waveform (Lt+Rt) obtained by adding the current waveform (Lt) and the current waveform (Rt) for each of the second virtual electrodes, indicates normal conduction of the neural activity current. Thus, by adding to each other the current waveforms of the plurality of second virtual electrodes corresponding to each of the first virtual electrodes, a normal current waveform can be obtained. Thus, if at least one of the current waveform (Lt) or the current waveform (Rt) is not normal, the current waveform (Lt+Rt) can be used to diagnose whether the nerve in the palmar part of the carpal tunnel is compressed.

In FIG. 4, an example in which two current waveforms (Lt) and (Rt) are added to each other is illustrated. However, the number of current waveforms to be added to each other may be 3 or more. The inward current flows from the entire surrounding of the first virtual electrode in cross-section toward the first virtual electrode for each of the first virtual electrodes. Therefore, in addition to the two current waveforms (Lt) and (Rt), the current waveform of the inward current in the Z direction of FIG. 2 may be added. At this time, the inward current in the Z direction may be the sum of the inward currents (absolute values) in the positive direction and in the negative direction toward the first virtual electrode.

FIG. 5 is a diagram illustrating an example of a change in the current waveform of the inward current in the cubital tunnel when a stimulation is applied to the ulnar nerve of a subject (a healthy person), and a summed waveform. For the same elements as in FIG. 4, the detailed description is omitted. The elements superimposed on the X-ray image of the elbow of the subject P illustrated on the left side of FIG. 5 are similar to those in FIG. 4. For example, numbers from 0 to 8 applied to virtual electrodes of the row Rt indicate the electrode numbers indicating the association with a current waveform.

Also in FIG. 5, the second virtual electrodes are positioned in the cross-sectional direction of the nerve axon (each first virtual electrode). Thus, it is possible to generate a current waveform of an inward current along the cross-sectional direction of the nerve axon based on the current component of each second virtual electrode.

In the current waveform illustrated in FIG. 5, for example, the current waveform of the electrode number 2 of the row Lt is not normal because there is no peak observed. In contrast, the current waveform (Lt+Rt) obtained by adding to each other the current waveform (Lt) and the current waveform (Rt) for each of the second virtual electrodes, indicates normal conduction of the neural activity current. Thus, the current waveform (Lt+Rt) can be used to diagnose whether the nerve in the cubital tunnel is compressed, even if at least one of the current waveform (Lt) or the current waveform (Rt) is not normal.

FIG. 6 is a diagram illustrating an example of the change of the current waveform of the inward current in the palmar part of the carpal tunnel when a stimulation is applied simultaneously to the index finger and middle finger of the subject (patient), and the summed waveform. For the same elements as in FIG. 4, the detailed description is omitted.

In FIG. 6, there is variation in the presence of peak amplitude and conduction delay between adjacent second virtual electrodes in each of the current waveforms (Lt) and current waveforms (Rt) and the current waveforms are unstable. Therefore, it is difficult to determine the virtual electrodes between which a failure has occurred, in the current waveform (Lt) and the current waveform (Rt).

On the other hand, in the current waveform (Lt+Rt) in which the current waveform (Lt) and the current waveform (Rt) are added to each other for each of the second virtual electrodes, the element of the unstable current waveform is improved, and it is observed that there is a reduction in the peak of the amplitude and a conduction delay between the current waveform of electrode number 4 and the current waveform of electrode number 5, which is indicated by a dashed line frame. Therefore, the current waveform (Lt+Rt) enables the evaluation of the neural function.

Figure 7:
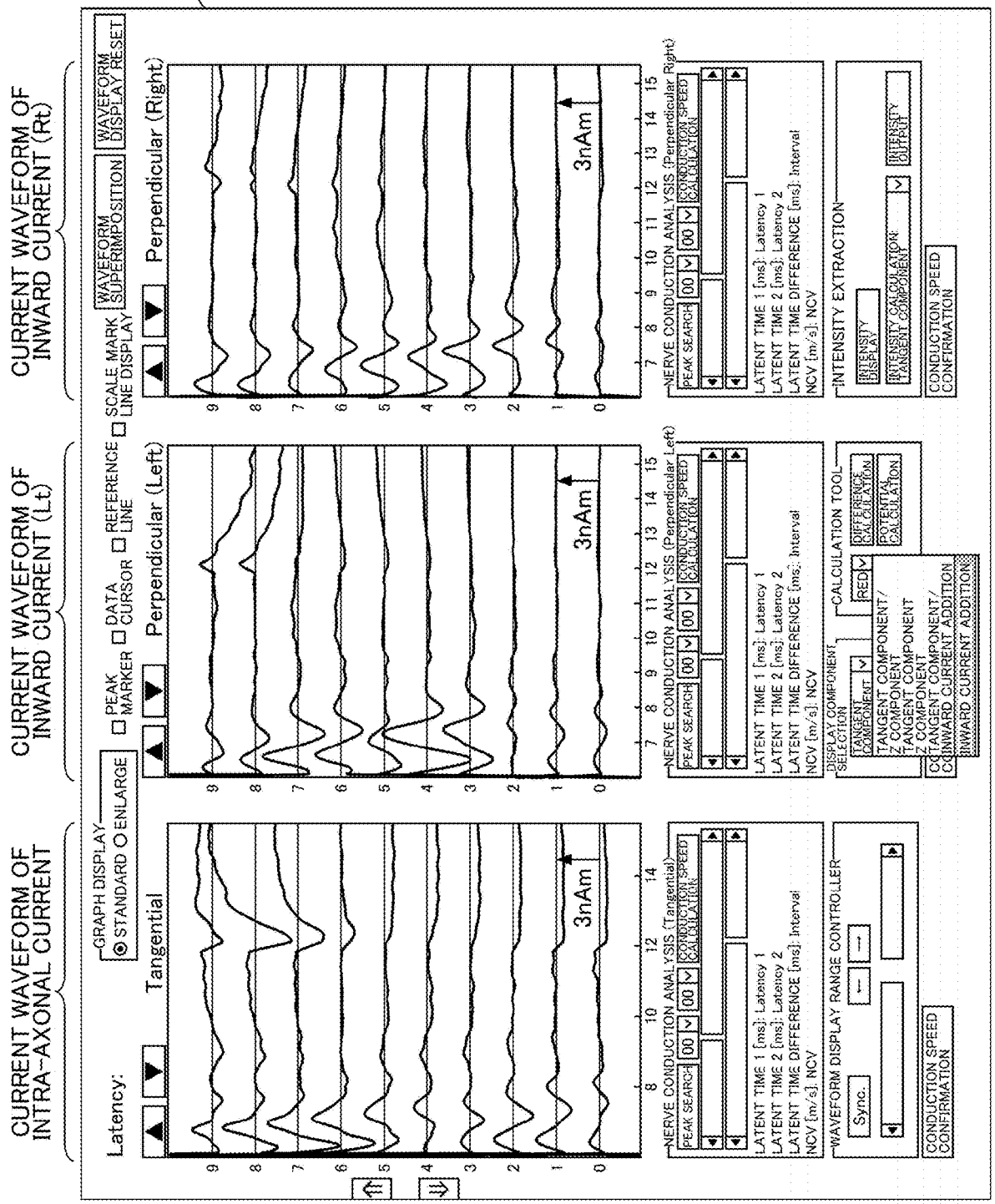
FIG. 7 is a diagram illustrating an example of a display window for selecting a current waveform to be displayed on the display device of FIG. 1 according to an embodiment of the present invention.

FIG. 7 is a diagram illustrating an example of a display window for selecting a current waveform displayed on the display device 40c of FIG. 1. In the example illustrated in FIG. 7, the current waveform of the intra-axonal current, the current waveform of the inward current (Lt), and the current waveform of the inward current (Rt) are displayed on the left, center, and right of the display window, respectively.

An instruction to display or hide a current waveform or to add a current waveform to the display window is received by displaying a pull-down menu by a user interface, such as the mouse 40a and the keyboard 40b, and having an instruction selected from the displayed pull-down menu. The current waveform in accordance with the instruction received from the pull-down menu is then re-displayed on the display window.

At least two of the current waveforms of the plurality of inward current waveforms displayed on the display window of the display device 40c, can be selected by using a user interface, such as a pull-down menu, to easily obtain the summed current waveform. An evaluator such as a doctor evaluating the neural function may determine the inward current to be selected while observing the current waveform of the plurality of inward currents displayed in the display window. This enables the evaluator to select a waveform of an appropriate inward current for the evaluation of neural function.

Figure 8:
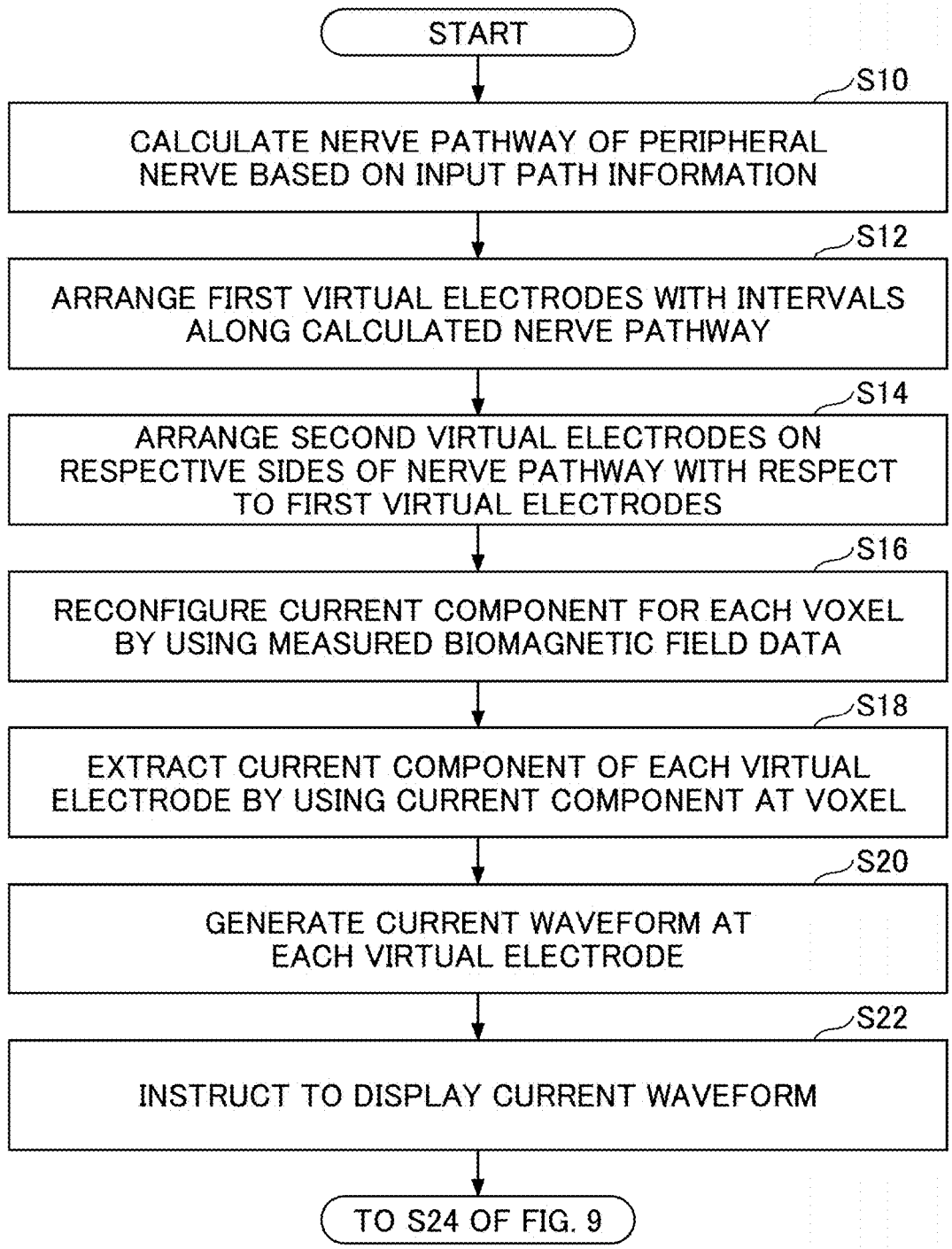
FIG. 8 is a flowchart illustrating an example of an operation of a calculating unit of FIG. 1 according to an embodiment of the present invention.
Figure 9:
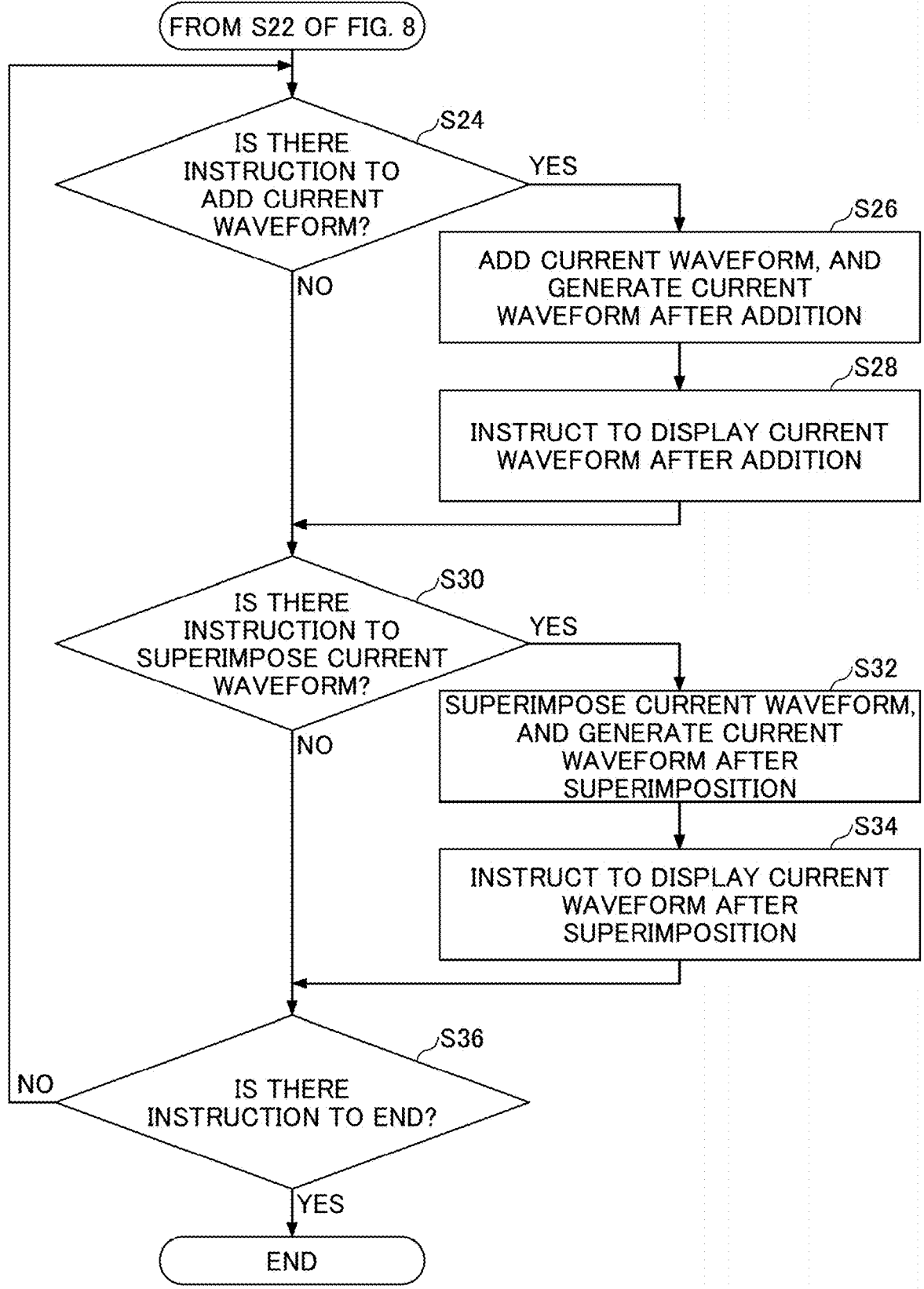
FIG. 9 is a flowchart illustrating a continuation of the operation of FIG. 8 according to an embodiment of the present invention.

FIGS. 8 and 9 are flowcharts illustrating an example of an operation of the calculating unit 520 of FIG. 1. The flow illustrated in FIGS. 8 and 9 illustrates an example of a control method of the data processing apparatus 50 and is implemented by a control program executed by a processor such as a CPU installed in the data processing apparatus 50.

First, in step S10, the path generating unit 521 of the calculating unit 520 calculates the nerve pathway of the peripheral nerve based on the path information received by the position input unit 511. For example, the position input unit 511 receives the coordinates of a plurality of positions on the image specified by an operator while viewing the morphological image displayed on the display device 40c, as the path information.

For example, the path generating unit 521 generates a Bezier curve along the nerve pathway from the coordinates at a plurality of positions specified by an operator, controls the image display unit 531, and displays the generated Bezier curve superimposed on the morphological image. Thus, the nerve pathway can be set to match the curved shape of the actual nerve axon or muscle fiber.

Next, in step S12, the virtual electrode generating unit 522 of the calculating unit 520 arranges a plurality of first virtual electrodes spaced apart on the path (that is, the nerve pathway) calculated by the path generating unit 521. The number and the arrangement interval of the first virtual electrodes are previously input via the mouse 40a, the keyboard 40b, or the like. Next, in step S14, the virtual electrode generating unit 522 of the calculating unit 520 arranges the second virtual electrodes on respective sides of the nerve pathway with respect to the first virtual electrode. Thus, the first virtual electrode and the second virtual electrode can be set at any position along the nerve pathway set by the path generating unit 521.

Next, in step S16, the reconfiguration analysis unit 523 of the calculating unit 520 reconfigures the current component for each voxel by using the biomagnetic field data of the subject P. Next, in step S18, the current extracting unit 524 of the calculating unit 520 extracts the current component of each virtual electrode by using the current component in the voxel calculated by the reconfiguration analysis unit 523 based on the positional relationship between each virtual electrode and the voxel. For example, the current extracting unit 524 extracts the current component in the first virtual electrode along the nerve pathway as the intra-axonal current and extracts the current component from the second virtual electrode directed toward the first virtual electrode on the nerve axon as the inward current.

Next, in step S20, the waveform calculating unit 525 of the calculating unit 520 generates an intra-axonal current in the first virtual electrode extracted by the current extracting unit 524 and a current waveform representing the change over time of an inward current in the second virtual electrode, respectively. Next, in step S22, the waveform calculating unit 525 outputs an instruction to display the generated current waveforms on the display device 40c, to the waveform display unit 532. Accordingly, the current waveforms of the intra-axonal current and the inward current are displayed in the display window on the screen of the display device 40c, as illustrated in FIG. 7.

Next, in step S24 of FIG. 9, the waveform calculating unit 525 determines whether an instruction to add current waveforms is given via the input control unit 510. When there is an instruction to add current waveforms, the waveform calculating unit 525 executes step S26, and when there is no instruction to add current waveforms, the waveform calculating unit 525 executes step S30. In step S26, the waveform calculating unit 525 adds the current waveforms based on the instruction to add current waveforms and generates the summed current waveform.

Next, in step S28, the waveform calculating unit 525 outputs an instruction to display the summed current waveform on the display device 40c to the waveform display unit 532. Thus, for example, as illustrated in FIGS. 4 to 6, the current waveform after addition is displayed on the display device 40c along with the current waveforms before addition. After step S28, the process proceeds to step S30.

In step S30, the waveform calculating unit 525 determines whether there is a superimposition instruction for superimposed display of the current waveforms via the input control unit 510. When there is a superimposition instruction, the waveform calculating unit 525 executes step S32, and when there is no superimposition instruction, the waveform calculating unit 525 executes step S36. In step S32, the waveform calculating unit 525 superimposes the current waveforms based on the superimposition instruction and generates the superimposed current waveform.

Next, in step S34, the waveform calculating unit 525 outputs an instruction to display the superimposed current waveform on the display device 40c to the waveform display unit 532. The waveform display unit 532 displays the current waveform superimposed by the waveform calculating unit 525 on the display device 40c, along with the current waveforms before superimposition. Thus, for example, the superimposed current waveform is displayed on the display device 40c along with the current waveforms before superimposition. After step S34, the process proceeds to step S36.

For example, the waveform calculating unit 525 superimposes the current waveform (Lt) and the current waveform (Rt) on each other, or superimposes the current waveform (Lt) and the current waveform (Lt+Rt) on each other, based on the external input. The number of current waveforms to be superimposed may be three or more. By superimposing and displaying the current waveforms on the display device 40c, the evaluator can visually recognize the degree of difference between the plurality of current waveforms. As a result, for example, the evaluator can select the current waveforms to be added to each other by referring to the superimposed current waveforms.

Next, in step S36, the waveform calculating unit 525 determines whether an instruction to end the addition or superimposition of the current waveforms is given via the input control unit 510. When there is an instruction to end the addition or superimposition, the waveform calculating unit 525 ends the process illustrated in FIG. 8 and FIG. 9, and when there is no instruction to end the addition or superimposition, the waveform calculating unit 525 returns to the processing of step S24.

Figure 10:
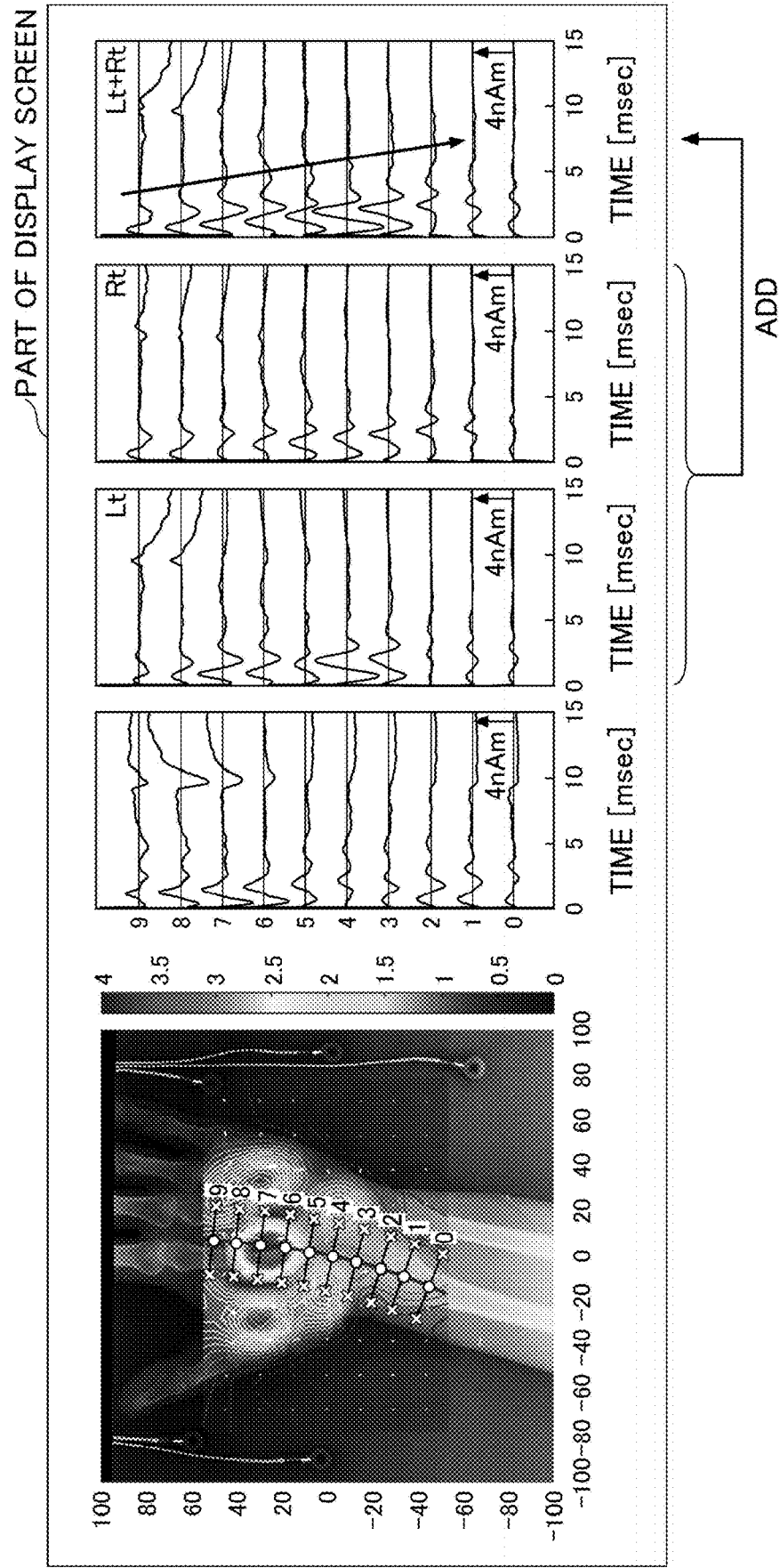
FIG. 10 illustrates an example of a morphological image and a current waveform before and after addition displayed on the display screen of the display device of FIG. 1 according to an embodiment of the present invention.
Figure 11:
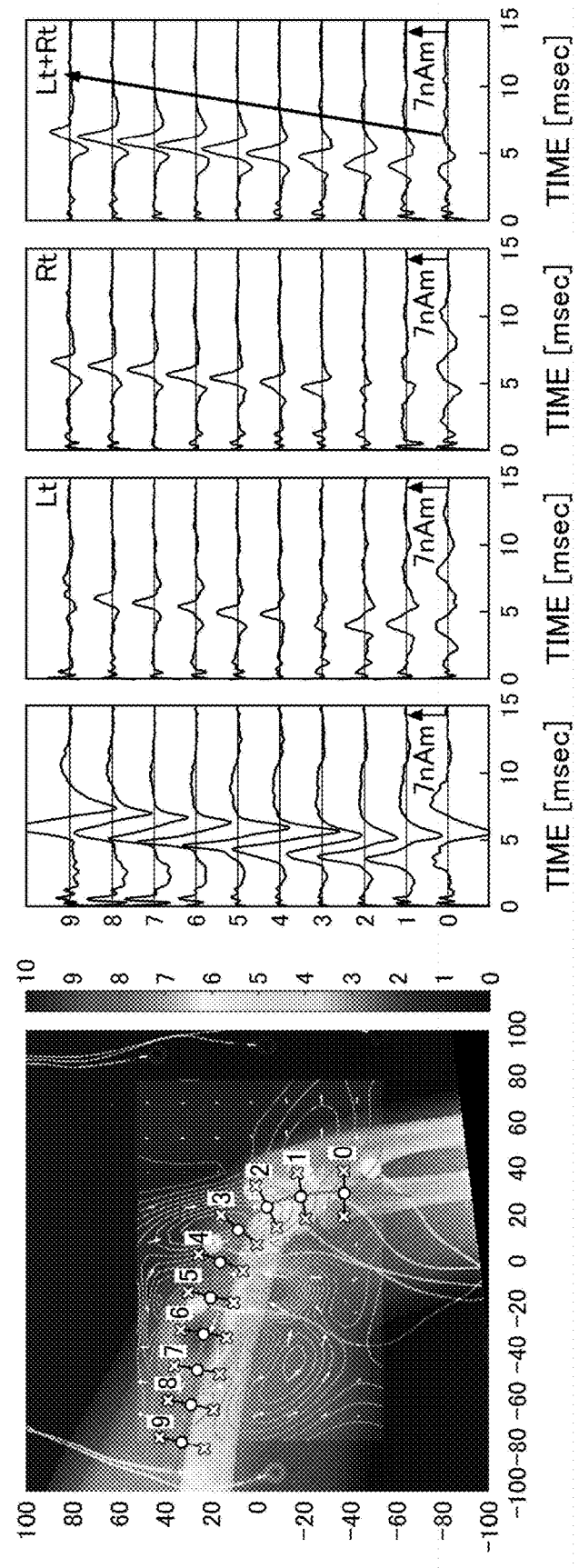
FIG. 11 illustrates another example of a morphological image and a current waveform before and after addition displayed on the display screen of the display device of FIG. 1 according to an embodiment of the present invention.

FIG. 10 and FIG. 11 are diagrams illustrating an example of a morphological image and current waveforms before and after summing displayed on a display screen of the display device 40c of FIG. 1. FIG. 10 illustrates an example in which the current waveform of the intra-axonal current is displayed on the display screen, in addition to the morphological image and the current waveforms of the inward current illustrated in FIG. 4. FIG. 11 illustrates an example in which the current waveform of the intra-axonal current is displayed on the display screen, in addition to the morphological image and the current waveforms of the inward current illustrated in FIG. 5.

As illustrated in FIGS. 10 and 11, by displaying any current waveform selected by the external input on the display screen, for example, the summed current waveform (Lt+Rt) can be displayed side by side with the current waveforms (Lt) and (Rt) before addition. Thus, the evaluator can visually and easily recognize the current waveform before and after addition, and determine whether the current waveform after addition is appropriate.

Figure 12:
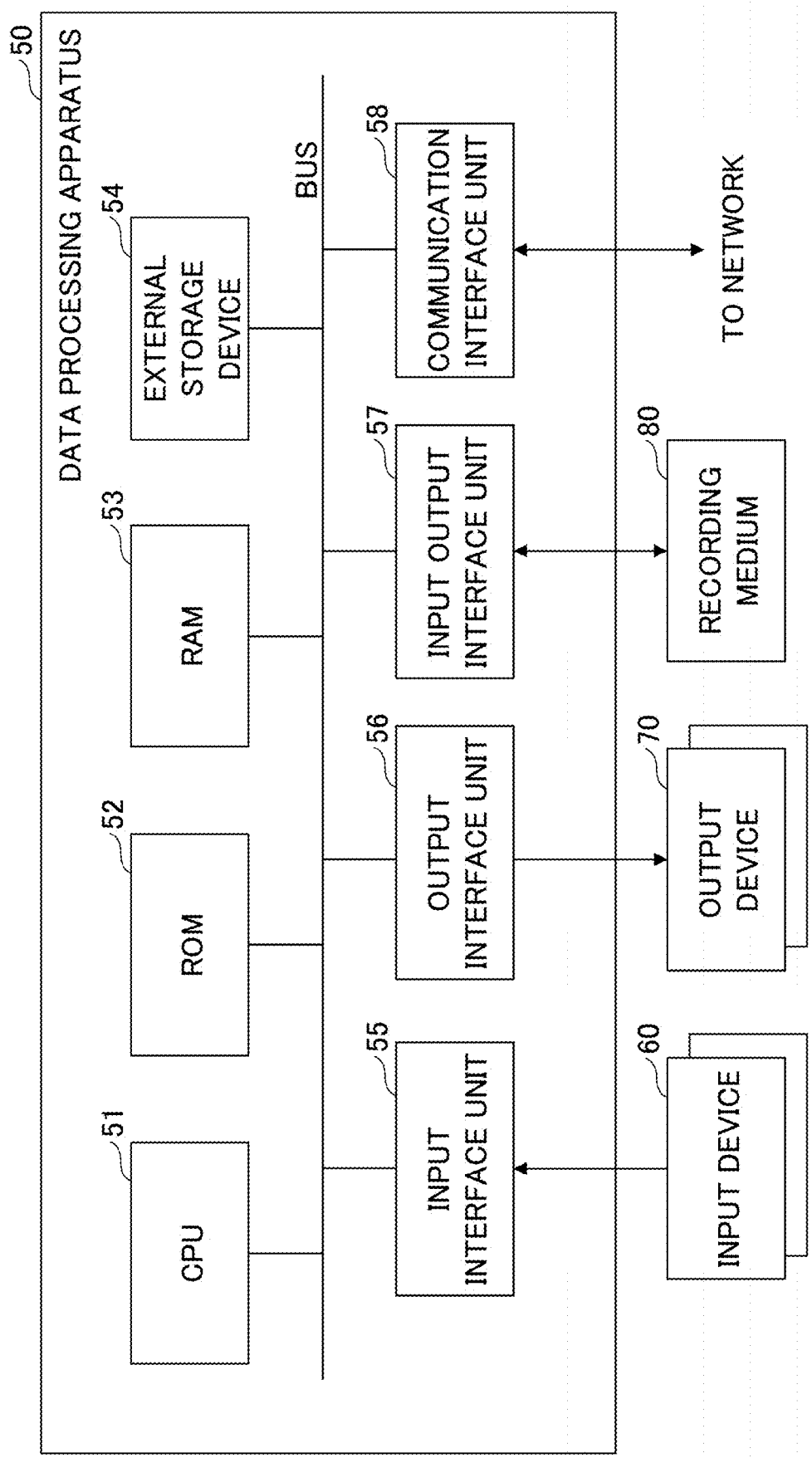
FIG. 12 is a block diagram illustrating an example of a hardware configuration of a data processing apparatus of FIG. 1 according to an embodiment of the present invention.

FIG. 12 is a block diagram illustrating an example of a hardware configuration of the data processing apparatus 50 of FIG. 1. The data processing apparatus 50 includes a central processing unit (CPU) 51, a read-only memory (ROM) 52, a random access memory (RAM) 53, and an external storage device 54. The data processing apparatus 50 includes an input interface unit 55, an output interface unit 56, an input output interface unit 57, and a communication interface unit 58. For example, the CPU 51, the ROM 52, the RAM 53, the external storage device 54, the input interface unit 55, the output interface unit 56, the input output interface unit 57, and the communication interface unit 58 are connected to each other via a BUS.

The CPU 51 executes various programs such as an OS (operating system) and an application and controls the overall operation of the data processing apparatus 50. The CPU 51 performs the control method of the data processing apparatus 50 which functions as the biomagnetic field measurement processing apparatus by executing the control program described above. The CPU 51 is an example of a computer that executes a control program.

The ROM 52 holds various programs and various parameters including a control program executed by the CPU 51. The RAM 53 stores various programs executed by the CPU 51 and data used in the programs. The external storage device 54 is a hard disk drive (HDD) or a solid state drive (SSD) or the like and stores various programs to be loaded in the RAM 53.

The input interface unit 55 is connected with an input device 60 that receives input from an operator or the like operating the data processing apparatus 50. For example, the input device 60 may be the mouse 40a or the keyboard 40b of FIG. 1, or a tablet or the like. An output device 70 for outputting various images, text, graphics, or the like, generated by the data processing apparatus 50 is connected to the output interface unit 56. For example, the output device 70 may be the display device 40c (FIG. 1), a printer, or the like, for displaying a display screen or the like generated by various programs executed by the CPU 51.

A recording medium 80, such as a USB (Universal Serial Bus) memory, is connected to the input output interface unit 57. For example, various programs such as a control program executed by the CPU 51 may be stored in the recording medium 80. In this case, various programs are transferred from the recording medium 80 to the RAM 53 via the input output interface unit 57. The recording medium 80 may be a compact disk read-only memory (CD-ROM), a Digital Versatile Disc (DVD, registered trademark), or the like. In this case, the input output interface unit 57 includes an interface that supports the recording medium 80 to be connected. The communication interface unit 58 connects the data processing apparatus 50 to a network or the like.

As described above, in the present embodiment, even when the current waveform of the second virtual electrode corresponding to the first virtual electrode is not normal, the current waveforms of at least two second virtual electrodes can be added to each other with respect to each of the first virtual electrodes to indicate a normal current waveform. Thus, a summed current waveform can be used for the diagnosis of whether a peripheral nerve of the palmar part of the carpal tunnel, the cubital tunnel, or the like is compressed. In this case, by placing the second virtual electrodes in a cross-sectional direction of each first virtual electrode, the current waveform of the inward current along the cross-sectional direction of the nerve axon or muscle fiber can be generated based on the current component of each second virtual electrode.

Further, at least two of the plurality of inward current waveforms displayed in the display window of the display device 40c can be selected by using a user interface such as a pull-down menu, such that the summed current waveform can be easily obtained. The evaluator of a neural function can determine the inward current to be selected while viewing the current waveforms of the plurality of inward currents, and, therefore, the evaluator can select the current waveform of the inward current appropriate for the evaluation of neural function.

Further, by displaying any current waveform selected by the external input on a display screen, for example, the summed current waveform (Lt+Rt) can be displayed side by side with the current waveforms (Lt) and (Rt) before addition. Thus, the evaluator can visually and easily recognize the current waveforms before and after addition, and determine whether the current waveform after addition is appropriate.

By superimposing the current waveforms, the evaluator can visually recognize the degree of difference between the plurality of current waveforms. As a result, for example, the evaluator can select the current waveforms to be added to each other by referring to the superimposed current waveforms.

The path generating unit 521 can set the nerve pathway according to the curved shape of the actual nerve axon or muscle fiber. Further, the virtual electrode generating unit 522 can set the first virtual electrode and the second virtual electrode at any position along the nerve pathway set by the path generating unit 521. This allows the current extracting unit 524 to extract the current waveform at any position along the shape of the nerve axon or muscle fiber.

According to one embodiment of the present invention, even when the current waveform of the inward current is distorted by the influence of the tissue around the part to be evaluated, it is possible to generate a current waveform of the inward current that can be used to correctly evaluate the nerve function or the muscle function.

The biomagnetic field measurement processing apparatus, the biomagnetic field measurement system, and the control method of the biomagnetic field measurement processing apparatus are not limited to the specific embodiments described in the detailed description, and variations and modifications may be made without departing from the spirit and scope of the present invention.

What is claimed is:

1. A biomagnetic field measurement processing apparatus comprising:
    circuitry;
    and a memory storing computer-executable instructions that cause the circuitry to execute:
    reconfiguring a current signal from a biomagnetic field signal measured from a subject;
    calculating a path of a nerve axon or a muscle fiber in a morphological image of the subject, wherein the morphological image is displayed on a display device
    generating plurality of first virtual electrodes positioned along the path and a plurality of second virtual electrodes on respective sides of the path with respect to each of the plurality of first virtual electrodes;
    extracting current waveforms of a plurality of inward currents that are current components directed toward the nerve axon or the muscle fiber from around the nerve axon or around the muscle fiber from the current signal, wherein the current waveforms are extracted at the plurality of second virtual electrodes and comprises at least a first current waveform and a second current waveform;
    generating a summed current waveform to be displayed on the display device by adding to each other the first current waveform extracted at one second virtual electrode of the plurality of second virtual electrodes on one side of the path and the second current waveform extracted at a corresponding second virtual electrode on an opposite side of the path than the one second virtual electrode at which the first current waveform was extracted;
    and displaying the summed current waveform together with to the first current waveform and the second current waveform in a user interface on the display device in order to evaluate neural function or muscle function.

2. The biomagnetic field measurement processing apparatus according to claim 1, wherein the plurality of inward currents are current components directed toward the nerve axon from around the nerve or around the muscle fiber are directed along a cross-sectional direction of the nerve axon or the muscle fiber.

3. The biomagnetic field measurement processing apparatus according to claim 1, wherein the circuitry is further caused to execute:

receiving a selection of the first current waveform and the second current waveform from among the current waveforms of the plurality of inward currents, said selection being made by external input.

4. A biomagnetic field measurement system comprising:
a magnetometer configured to measure a biomagnetic field from a subject;
a display device;
and a biomagnetic field measurement processing apparatus, wherein the biomagnetic field measurement processing apparatus includes:
circuitry;
and a memory storing computer-executable instructions that cause the circuitry to execute:
reconfiguring a current signal from the biomagnetic field signal;
calculating a path of a nerve axon or a muscle fiber in a morphological image of the subject, wherein the morphological image is displayed on the display device
generating plurality of first virtual electrodes positioned along the path and a plurality of second virtual electrodes on respective sides of the path with respect to each of the plurality of first virtual electrodes;
extracting current waveforms of a plurality of inward currents that are current components directed toward the nerve axon or the muscle fiber from around the nerve axon or around the muscle fiber from the current signal, wherein the current waveforms are extracted at the plurality of second virtual electrodes and comprises at least a first current waveform and a second current waveform;
generating a summed current waveform to be displayed on the display device by adding to each other the first current waveform extracted at one second virtual electrode of the plurality of second virtual electrodes on one side of the path and the second current waveform extracted at a corresponding second virtual electrode on an opposite side of the path than the one second virtual electrode at which the first current waveform was extracted;
and displaying the summed current waveform together with the first current waveform and the second current waveform in a user interface on the display device in order to evaluate neural function or muscle function.

5. A control method of a biomagnetic field measurement processing apparatus, the control method comprising:
reconfiguring a current signal from a biomagnetic field signal measured from a subject;
calculating a path of a nerve axon or a muscle fiber in a morphological image of the subject, wherein the morphological image is displayed on a display device
generating plurality of first virtual electrodes positioned along the path and a plurality of second virtual electrodes on respective sides of the path with respect to each of the plurality of first virtual electrodes;
extracting current waveforms of a plurality of inward currents that are current components directed toward the nerve axon or the muscle fiber from around the nerve axon or around the muscle fiber from the current signal, wherein the current waveforms are extracted at the plurality of second virtual electrodes and comprises at least a first current waveform and a second current waveform;
generating a summed current waveform to be displayed on the display device by adding to each other the first current waveform extracted at one second virtual electrode of the plurality of second virtual electrodes on one side of the path and the second current waveform extracted at a corresponding second virtual electrode on an opposite side of the path than the one second virtual electrode at which the first current waveform was extracted;
and displaying the summed current waveform together with the first current waveform and the second current waveform in a user interface on the display device in order to evaluate neural function or muscle function.

6. A non-transitory computer-readable recording medium storing a program that causes a computer to execute a process included in the control method according to claim 5.

* * * * *